March 27, 1951 E. E. DOERSCHLER Re. 23,348

WALKER

Original Filed Aug. 2, 1949

INVENTOR.
Edgar E. Doerschler
BY
Scrivener & Parker
ATTORNEYS

Reissued Mar. 27, 1951

Re. 23,348

UNITED STATES PATENT OFFICE 23,348

WALKER

Edgar E. Doerschler, Takoma Park, Md.

Original No. 2,526,205, dated October 17, 1950, Serial No. 108,107, August 2, 1949. Application for reissue January 2, 1951, Serial No. 203,850

2 Claims. (Cl. 128—94.5)

Matter enclosed in heavy brackets [ ] appears in the original patent but forms no part of this reissue specification; matter printed in italics indicates the additions made by reissue.

This invention relates to devices for supporting the leg on the ground during walking to permit improved ambulation after fracture or medical or other treatment and while the leg and foot are encased in a cast.

In the treatment of fractures of the leg it is customary at this time to require ambulation as soon as possible after setting and while the leg and foot are encased in a cast which prevents movement at the joints. Heretofore this has been effected by supporting the fractured and cast-encased leg on the ground by means of a U-shaped iron stirrup or "walking iron," the upright arms of which are positioned on opposite sides of the leg and embedded in a plaster-impregnated bandage which encases the foot and leg and prevents relative movement of the bone of the foot and leg, whether fractured or not. It has heretofore been proposed to provide an improved type of "walker" to replace the walking iron and this improved walker comprises a device having a flat upper surface on which part of the sole of the foot rests and an arcuate lower surface which rests on the ground. In theory such a device presents many advantages over the walking iron, principally in that it should permit simulation of the normal rocking motion of the ankle in walking without permitting actual relative movement of the ankle bones. In practice the walkers of this type which have been proposed have not been useful or satisfactory and have not replaced the walking iron despite the many disadvantages of the latter device.

My invention has to do with walkers of the proposed type described above but differs in many material respects from those which are known, whereby it is successful and useful. The walker which I have invented and which is disclosed and claimed in this application comprises a solid, unitary device having a flat upper surface receiving the sole of the foot and a curved lower ground-engaging surface the curvature of which is such that the patient is permitted to take a full normal step without the interrupting twisting motion of the leg which is necessary when the walking iron is used. This specially-shaped walking surface is extended forwardly to the metatarso-phalangeal joint, thus providing complete support to the foot and, at the same time, protecting the distal end of the cast from wear and breakage and insuring full and continuous immobilization of the tarsal and metatarsal bones. In addition, the walking surface is so constructed that the highest point thereof is so disposed that it will normally, when in use, be positioned directly below and in the prolongation of the weight-bearing axis A of the leg, thus taking best advantage of the normal movement of the leg in walking. Because of the arrangement and proportions of its parts, the walker is easily adaptable to any degree of planter or dorsoflexion of the foot which may be required in treatment. This may be accomplished by building up with plaster or other material under the heel or toe.

A further and most important result of my invention is the provision of a walker of the described type having greatly improved means for attachment to the cast. This is provided by means of apertures which are so placed that attaching wires and bandages may be most advantageously used to attach the walker to the cast, and also by the structure of the walker by virtue of which the cast, when hardened, grasps and supports the walker thus supplementing the supporting action of the wires and bandages.

Another important result of my invention has been the provision of a walker of the described type which may be so cheaply manufactured that it may be classified as "expendable" rather than as "salvageable." This is effected by forming the walker as a solid block which may be easily cast or molded of rubber, plastic, wood pulp or other appropriate material. Other useful and important results of my invention will be made apparent by the following description and the annexed drawing of one form which my invention may take.

Referring to the drawings in which similar reference numerals refer to like parts, Fig. 1 is a side view of my improved walker applied to the foot of the user;

Figure 1:
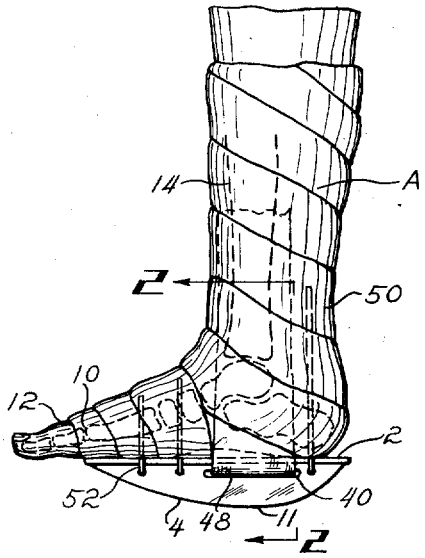
Figure 2:
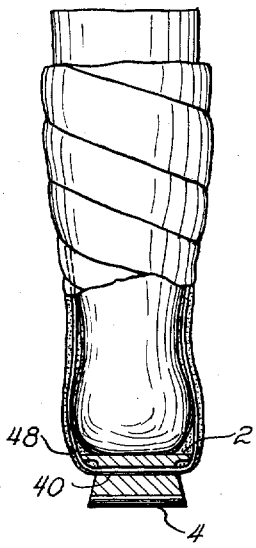
Fig. 2 is a rear view thereof, partly in section, taken on lines 2—2 of Fig. 1.
Figure 3:
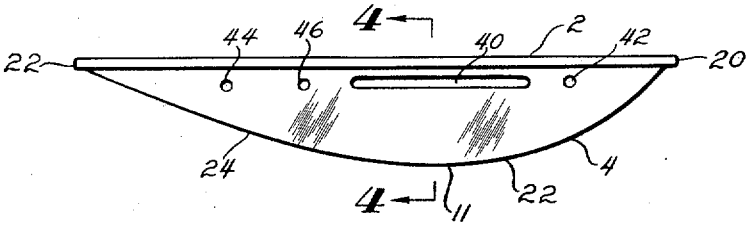
Fig. 3 is a side view of my improved walker.
Figure 4:
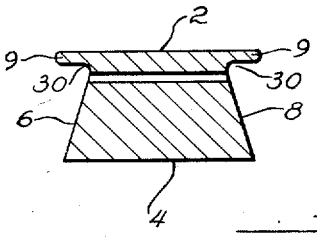
Fig. 4 is a sectional view taken on the lines 4—4 of Fig. 3.

The improved walker provided by my invention, one form of which is illustrated in the drawing, comprises a solid, unitary block formed, cast or molded into the shape provided by the invention and therefore having a substantially flat upper surface 2 on which the sole part of the cast rests, a lower ground-engaging surface 4 having a generally arcuate surface which will be described more fully hereinafter, and side walls 6, 8 which converge from the lower surface 4 upwardly toward but not to, the upper surface 2, leaving over-hanging side parts 9 at the opposite sides of the walker. The walker is preferably made in different lengths to be used with feet of different length and, in accordance with the teaching of the invention the upper surface is of such length that its rearward end lies just below the rearmost extremity of the heel and its forward end lies just below the metatarso-phalangeal joint which is indicated at 10 in Fig. 1. This distal extension of the walker is used in all cases in which the metatarsal or phalangeal bones are not involved in the fracture and therefore in such cases extends to the distal end 12 of the cast.

If the metatarsal or phalangeal bones are involved in the fracture the cast is usually extended to cover the toes and in such cases the walker is extended to the same length distally. In this modified form of the invention the structure of the walker is not changed in any way, the only modification being the change in the length thereof.

An important feature of the invention has to do with the configuration of the lower, ground-engaging surface of the walker. As stated hereinbefore, this lower surface is generally arcuate in shape. In accordance with the invention, this arcuate shape is such that the highest, i. e. most extended point 11 of the area is just below the medial line extending through the tibia 14, which line is indicated at A in Fig. 1 and is known as the "weight-bearing" line of the leg. The walking surface 4 has such a shape that the deepest part 11 thereof is much closer to the rear end 20 of the walker than to the front end 22. Thus, the rearward part 22 of the walking surface is shaped as an arc having a relatively short radius, while the forward part 24 of the walking surface is shaped as an arc having a longer radius. By placing the deepest part of the walker below the weight-bearing line and by shaping the walking surface in the described manner, it is possible to achieve a normal rocking movement of the foot and leg without requiring the twisting movement which normally accompanies the use of a walking iron.

Means are provided by the invention for securely attaching the walker to the sole part of the cast in which the fractured foot and leg are encased. In the usual treatment of such leg and foot fractures, the leg and foot are wrapped with plaster-impregnated bandage and the plaster is allowed to harden, thus making a cast in which the leg and foot are held immobile. As stated hereinbefore, the upper part of the walker overhangs the side walls, because of the upward convergence of the side walls, thus providing a recess 30 at each side of the walker and beneath the upper surface within which plaster and bandage forming part of the cast may be forced while wet, and then allowed to dry in order to provide a secure attachment between the cast and the walker. Means are also provided by the invention for more securely attaching the cast and the walker and such means comprise a plurality of openings extending laterally through the walker and adapted to receive wires and bandage splints. In the preferred form of the invention an elongated opening 40 extends laterally through the walker just below the upper surface thereof and is preferably disposed equi-distantly on either side of the deepest part 11 of the walker. Rearwardly of this elongated opening a small, preferably circular opening 42 extends laterally through the walker, while forwardly of the opening 40 there is provided a plurality of small, preferably circular openings 44, 46. The elongated opening 40 is provided for the purpose of receiving a plaster-impregnated bandage 48 which is led therethrough and thence upwardly along the opposite sides of the leg beneath or through some or all of the convolutions 50 of the bandage. The openings 42, 44, 46 are provided for the purpose of receiving wires 52 which are led therethrough and thence upwardly along the sides of the leg beneath or through one or more of the convolutions of the bandage.

In the use and application of my improved walker in connection with a fracture which, it will be assumed, does not involve the metatarsal or phalangeal bones, the fractured leg is first encased in a preliminary layer of plaster-impregnated bandage. The flat upper surface of the walker is then applied to the sole part of the bandage-encased foot and is positioned thereon in the manner hereinbefore described. A plaster-impregnated bandage 48 is then led through the elongated opening 40 in the walker and/or one or more wires 52 are led through the various openings 42, 44, 46. The bandage 48 and the wires 42, 44, 46 are then led upwardly along the opposite sides of the foot and leg, after which additional plaster-impregnated bandages are wrapped about the foot and leg. While wet, the plaster which impregnates the bandage is pressed under the upper surface of the walker into the recesses 30 and, when this plaster hardens, it will provide an additional means for securely holding the parts together.

While I have described and illustrated one form of my invention, it will be apparent to those skilled in the art that other embodiments, as well as modifications thereof, may be made without departing in any way from the spirit or scope of the invention, for the limits of which reference must be made to the appended claims.

What is claimed is:

1. A solid, unitary walking support for the lower extremity of a cast-encased leg, having a substantially flat surface adapted to be placed under and in contact with the sole part of the cast, an outwardly-arcuate surface adapted to engage the ground and being substantially coextensive with the flat surface longitudinally thereof and having such a configuration that the most extended part thereof is closer to one end of the support than the other, and side walls converging from the arcuate surface toward but not to the flat surface leaving an overhanging part at each side of the support extending longitudinally of the support.

2. A unitary walking support for the lower extremity of a cast-encased leg, comprising a solid body having a substantially flat surface adapted to be placed under and in contact with the sole part of the cast, an outwardly-arcuate surface adapted to engage the ground and being coextensive with the flat surface longitudinally thereof and having such a configuration that the most extended part thereof is closer to one end of the support than the other, [said arcuate surface having an elongated aperture laterally through the support extending substantially equal distances longitudinally of the most extended part of the arcuate surface and having at least one additional aperture laterally through the support,] *said body having a transverse aperture therethrough which is elongated longitudinally of the body and extends substantially equidistantly on opposite sides of said most extended part of the arcuate surface and having at least one additional aperture extending laterally therethrough,* said apertures being adapted to receive means for attaching the support to the cast.

EDGAR E. DOERSCHLER.

REFERENCES CITED

The following references are of record in the file of this patent or the original patent:

Zentralblatt fur Chirurgie for 1934, pp. 1726–1729.

Zimmer Fracture Equipment, a catalog of the Zimmer Manufacturing Company, of Warsaw, Indiana, issued February 1, 1947, pp. 116–117.